United States Patent [19]
Van Praet

[11] Patent Number: 5,783,451
[45] Date of Patent: Jul. 21, 1998

[54] PIPETTING UNIT AND METHOD FOR LIQUIDS

[76] Inventor: Peter Van Praet, Bergenstraat 49, 3053 Hassrode, Belgium

[21] Appl. No.: 782,820

[22] Filed: Jan. 13, 1997

Related U.S. Application Data

[63] Continuation of Ser. No. 417,952, Apr. 6, 1995, abandoned.

[30] Foreign Application Priority Data

Apr. 15, 1994 [BE] Belgium ............................. 09400392

[51] Int. Cl.⁶ .................................. G01N 1/10; G01N 1/14
[52] U.S. Cl. .......................... 436/180; 436/179; 422/100; 422/104; 73/864.13; 73/864.14; 73/864.15
[58] Field of Search .......................... 422/99, 100, 104; 436/179, 180; 73/864.13, 864.14, 864.15, 864.16

[56] References Cited

U.S. PATENT DOCUMENTS

| | | | |
|---|---|---|---|
| 3,665,980 | 5/1972 | Croslin et al. | 141/183 |
| 4,298,575 | 11/1981 | Berglund | 73/864.13 |
| 4,399,711 | 8/1983 | Klein | 73/864.16 |
| 4,399,712 | 8/1983 | Oshikubo et al. | 73/864.16 |
| 4,554,134 | 11/1985 | Tervamaki et al. | 422/100 |
| 4,760,939 | 8/1988 | Ball et al. | 222/23 |
| 5,055,263 | 10/1991 | Meltzer | 422/65 |
| 5,104,624 | 4/1992 | Labriola | 422/100 |
| 5,304,766 | 4/1994 | Baudet et al. | 219/687 |
| 5,320,810 | 6/1994 | Al-Mahareeq et al. | 422/100 |

Primary Examiner—Harold Y. Pyon
Attorney, Agent, or Firm—Breiner & Breiner

[57] ABSTRACT

A method and system for accurate aspiration and dispensing of fluids and comprising in combination a volumetric pump, a motor, a motor driver, an encoder (device used to measure angular displacements) and a computing unit.

7 Claims, 3 Drawing Sheets

| SUCTION STROKE | NULL POINT (CROSS OVER) | DISCHARGE STROKE | NULL POINT (CROSSOVER) |
|---|---|---|---|
| 1 | 2 | 3 | 4 |

FIG. 8
FIG. 9
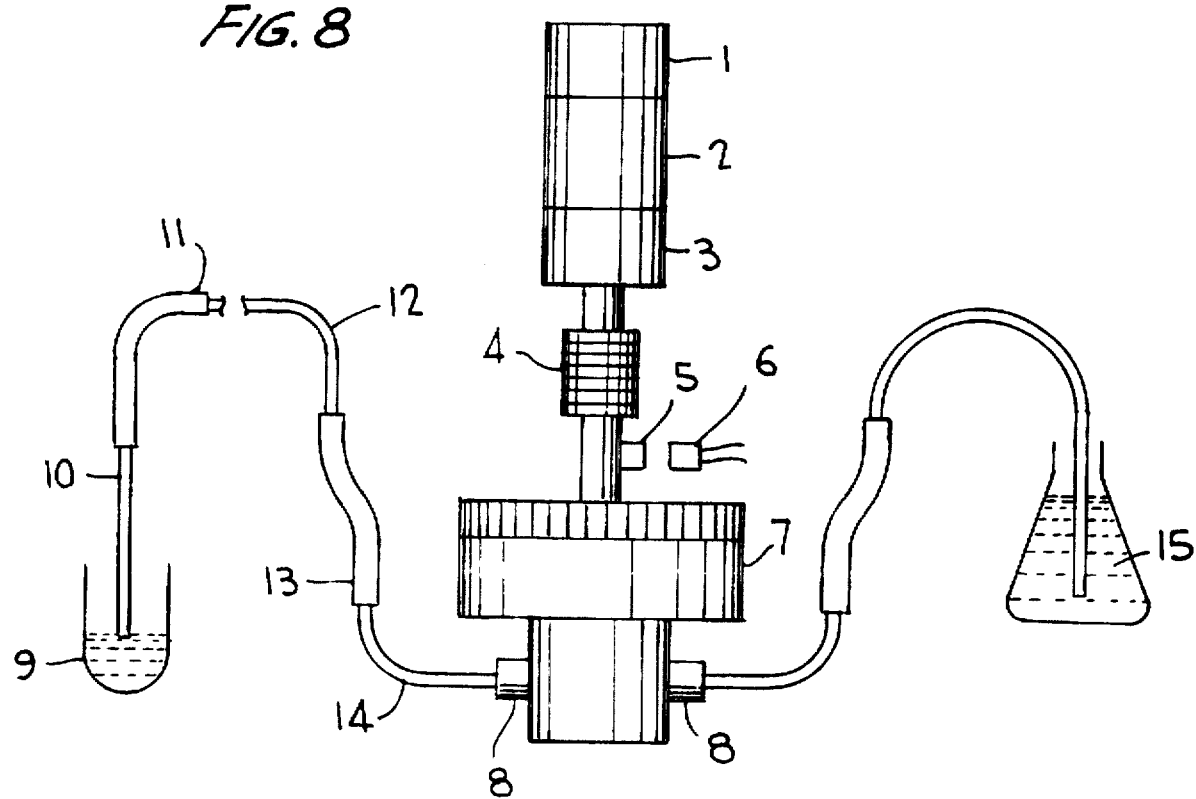
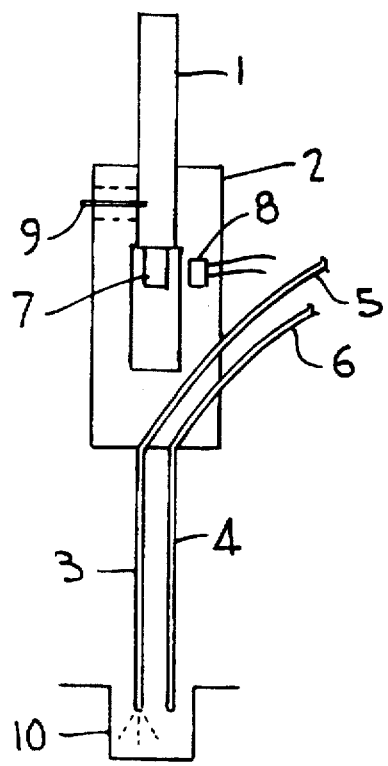

PIPETTING UNIT AND METHOD FOR LIQUIDS

This is a continuation of application Ser. No. 08/417,952 filed on Apr. 6, 1995, now abandoned.

FIELD OF INVENTION

The present invention relates to a unit for accurately aspirating and dispensing liquids and more specifically to a pipetting device provided with a volumetric pump.

BACKGROUND OF INVENTION

It is known that valveless volumetric pumps can be used in the laboratory environment to accurately manipulate fluids. An example of this kind of pump is manufactured by Fluid Metering Inc., 29 Orchard Street, Oysterbay, N.Y. 11771. Such a pump and its operation is shown in FIG. 1 of the drawing.

Thus, the valveless pumping action is achieved by rotating and synchronously moving the piston up and down in an accurately ground cylinder. There is an aspiration and a dispensing stroke during each cycle. A flat piece of the cylinder is used to transport the fluid from the input to the output port of the pump. The tilt angle between the piston axis and the axis of the pumphouse is adjustable as shown in FIG. 3, denoted as 6 in the drawing and allows an adjustment of the displaced volume per revolution (later referred to as the "one shot volume"). The relation between the liquid FLOW and the rotation ANGLE is approximately sinusoidal as shown in FIG. 2. The total displaced volume is easily calculated by simply multiplying the one shot volume by the total number of rotations of the shaft. This is the way the pump is normally used.

OBJECTS AND SUMMARY OF INVENTION

A primary object of the present invention is to use a pump to displace volumes of fluid many times smaller than displaced in a one shot volume.

This invention provides a pump arrangement that allows accurate aspiration and dispensing of fluids and consists of a volumetric pump, a motor, a motor driver, an encoder device which measures angular displacements and a computing unit.

BRIEF DESCRIPTION OF THE DRAWING

In the drawing,

FIG. 4b illustrates liquid FLOW corresponding with the same shaft rotation as 4a;

FIG. 8 illustrates an example of a setup; and

FIG. 9 illustrates a second representative set up.

DETAILED DESCRIPTION OF THE INVENTION

Figure 1:
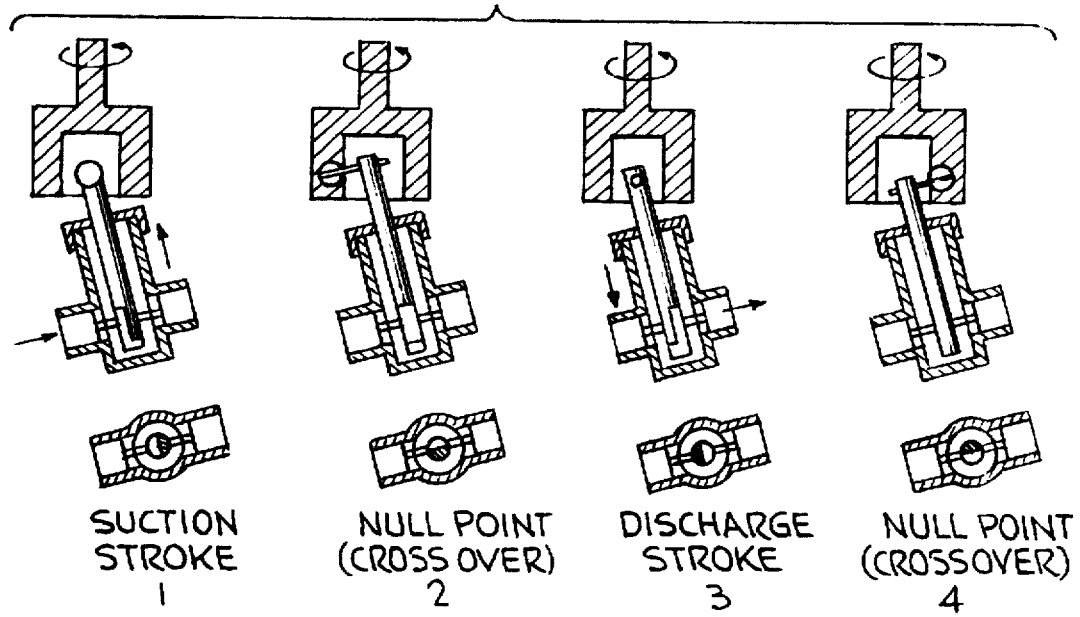
FIG. 1 illustrates the operation of the valveless volumetric pump known in the prior art.
Figure 2:
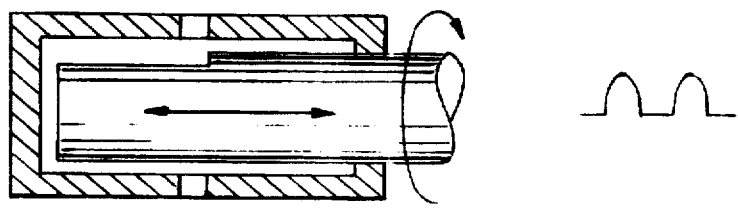
FIG. 2 is a cross section of the piston/cylinder of a volumetric pump and illustration of the pulsating nature of the liquid flow.
Figure 3A:
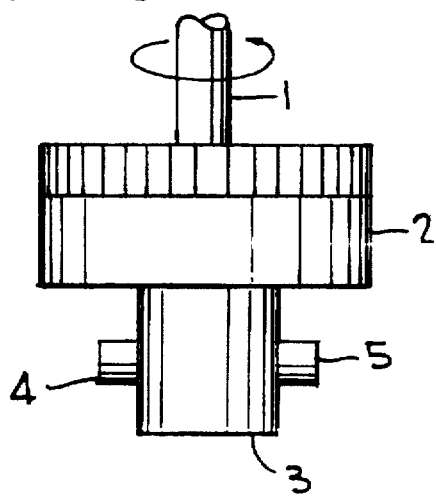
FIGS. 3a and 3b illustrate the different parts of the pump in the tilted and non-tilted position.
Figure 3B:
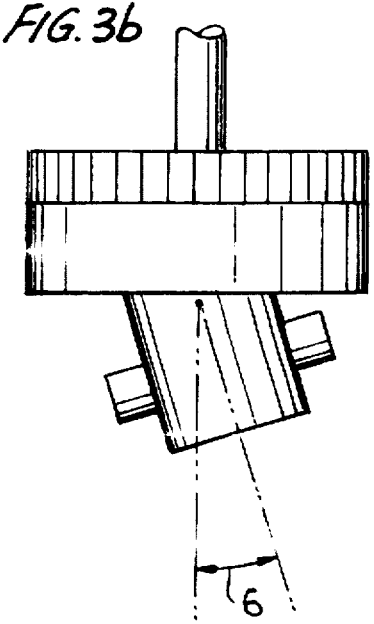

A volumetric pump, driven by an electric motor, is used to displace a fluid. The displaced volume is a function of the rotation of the shaft (FIG. 3.1) and the tilt angle (FIG. 3.6). The tilt angle can be adjusted by rotating an adjustment ring (FIG. 3.2). The direction of rotation of the shaft (FIG. 3.1) causes the liquid to flow from the input to the output (FIGS. 3.3 and 3.4) or vice versa.

Figure 4A:
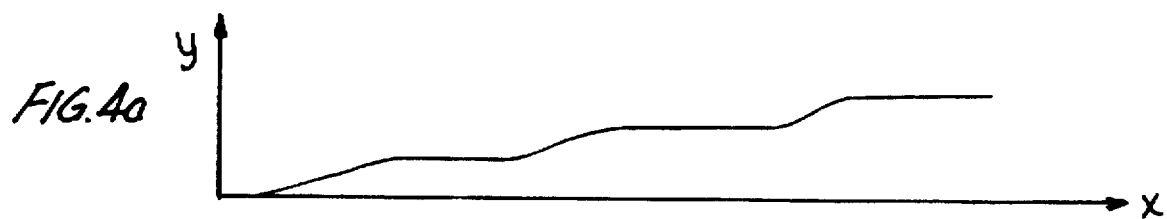
FIG. 4a illustrates the total displaced volume as a function of the shaft rotation.
Figure 4B:
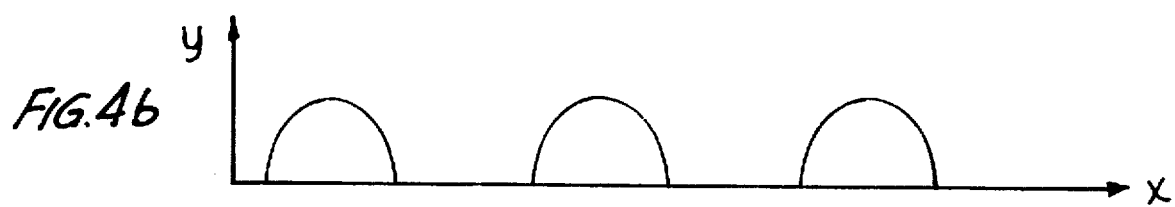

The adjustment ring (FIG. 3.2) enables the calibration of the one shot volume. As an example, assume an one shot volume of 20 uL where uL=micro liter. FIG. 4a shows the total displaced volume (y-axis) as a function of the number of revolutions (x-axis) of the shaft. FIG. 4b shows the FLOW (y-axis) as a function of the number of revolutions (x-axis) of the shaft.

Procedure for Displacing 100 uL

Figure 5:
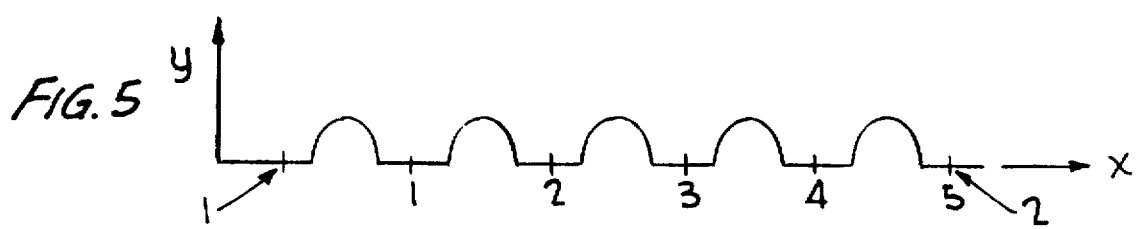
FIG. 5 illustrates that the displaced volume equals 100 uL.

The one shot volume is calibrated to be 20 uL by adjusting the calibration ring (FIG. 3.2). The shaft should make 5 turns to totalise a displaced volume of 100 uL. FIG. 5 illustrates the flow (y-axis) as a function of the number of revolutions (x-axis). The start (FIG. 5.1) and stop (FIG. 5.2) positions are also indicated.

Procedure for Displacing 70 uL

Figure 6:
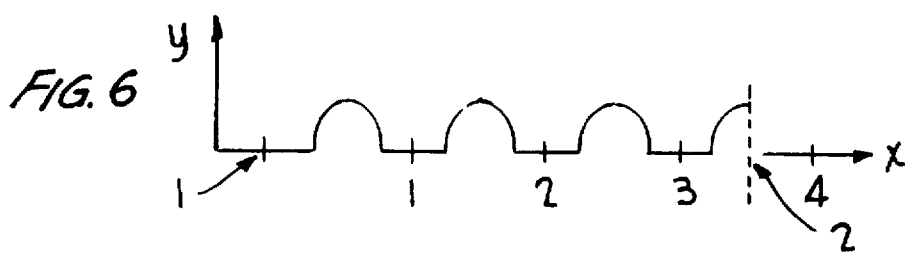
FIG. 6 illustrates that the displaced volume equals 70 uL.

The shaft should make three and a half turns. FIG. 6 illustrates the flow (y-axis) as a function of the number of revolutions (x-axis). The start (FIG. 6.1) and stop (FIG. 6.2) positions are also indicated.

Procedure for Displacing 33 uL

Figure 7:
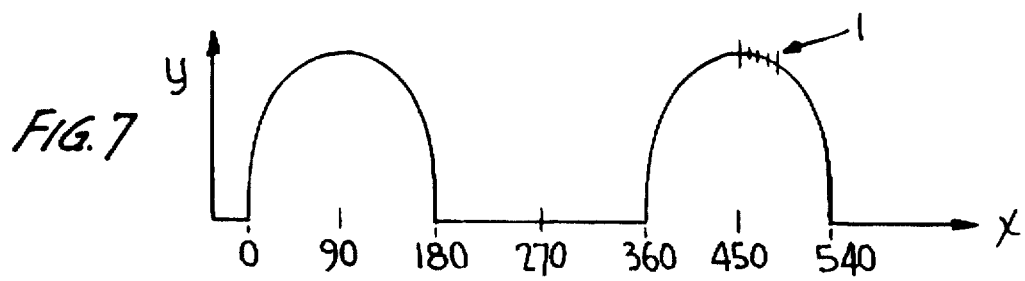
FIG. 7 illustrates that the displaced volume equals 33 uL.

FIG. 7 shows the liquid flow as a function of the rotation of the shaft. This rotation is expressed in degrees. First the shaft is rotated over 450 degrees. This corresponds to 30 uL. Now an additional small rotation is added. This angle is calculated by the computing unit using the remaining angle (3 uL) and the quasi-sinusoidal relationship between the angular displacement and the movement of the piston as inputs. In this example the starting position for displacing the remaining volume is the top of the sinus. This will not always be true. Other volumes may require other starting positions. In general, however, each volume can be divided into two parts. A first part being a multiple of the one shot volume, and a second part called the fraction volume.

FIG. 8 shows a possible arrangement for a pipetting device. The motor (FIG. 8.2) is equipped with a gearbox (FIG. 8.3) and an encoder (FIG. 8.1). The motor and the pump (FIG. 8.7) are connected via a coupling device (FIG. 8.4). The fluid connections are indicated (FIG. 8.8).

A magnet (FIG. 8.5)/Hall-sensor (FIG. 8.6) combination or another detection system is used to detect the reference position (see also FIG. 5.1) of the pump. A fluid originating from the container (FIG. 8.15) fills the complete path. When the pump starts working the whole fluid path starts to move, from the volume that should be picked-up (FIG. 8.9) to the fluid in the container (FIG. 8.15). The whole setup will not work if the path is filled with air. The compressibility of the air would generate large errors.

Description of the Fluid Path

The needle (FIG. 8.10) goes into the liquid (FIG. 8.9) that should be picked-up or dispensed. This needle is connected with the pump via a piece of silicone tubing (FIG. 8.11), a piece of Teflon tubing (FIG. 8.12) and an optional piece of silicone tubing (FIG. 8.13) used as a pressure pulse absorber. A piece of Teflon tubing (FIG. 8.14) connects this pulse absorber to the pump. Since the pump is allowed to turn in the opposite direction, the same elements can be found on the right hand side of the pump.

EXAMPLE 1

An example of a task that is commonly performed in clinical laboratories by a pipetting device is as follows:

Pick-up 100 uL of a diluent solution from container A (5 rotations CW). Pick-up 2 uL serum from container B (fraction of a rotation CW). Dispense both in container C (5 rotations+the fraction CCW). Container C holds now a 2/102 diluted sample of serum.

EXAMPLE 2

A procedure frequently performed in clinical laboratories is called "washing" of Microliter Wells and is as follows:

A Microliter Well is a small well with a typical volume of 300 uL. The task is to wash a Microliter Well using 1200 uL of wash solution. A needle (FIG. 9,3) is positioned above the well (FIG. 9,10) and causes the pump to accomplish 60 rotations. This equals 1200 uL (with a one shot volume of 20 uL). At the same time another needle (FIG. 9,4) aspirates the dispensed wash solution preventing the well from overflowing.

Emptying the well could be performed as follows (FIG. 9). A vertically mounted rod (FIG. 9,1) has at one end a house (FIG. 9,2) that holds two needles (FIG. 9,3) and (FIG. 9,4). This house is allowed to move up and down (with respect to the rod) over a short distance (e.g., one tenth of an inch). This movement is limited by a pin that is connected with the rod and goes through a hole in the house (FIG. 9,9).

The dispensing needle (FIG. 9,3) is connected to the pipetting unit via a small tube (FIG. 9,5). The aspirating needle (FIG. 9,4) is connected to an aspirating pump via another small piece of tubing (FIG. 9,6).

When the 1200 uL have been dispensed (the well is now washed), the aspirating pump keeps working and at the same time the rod starts moving down. At a certain moment the needles will touch the bottom of the well. The well is now completely empty. The rod continues its downward movement until the magnet (FIG. 9,7) is detected by the detector (FIG. 9,8). At that moment the downward movement of the rod stops. This bottom sensing method guarantees a nicely evacuated well.

It is claimed:

1. A method of pumping fluids using in combination a volumetric pump, a motor, a motor shaft, a motor driver, an encoder, and a computing unit operatively associated with a calculation unit, wherein movement of the shaft includes two simultaneous motions, a first motion of an up and down movement of the shaft to displace fluid in conjunction with a second motion of rotating the shaft thereby moving a volume of fluid from an input port to a separate output port, wherein movement of the shaft provides quasi-sinusoidal pulsed fluid volume discharges, the method comprising:

providing a reference position means to monitor rotational position of the motor shaft;

monitoring the rotational position of the shaft using the reference position means;

operating the calculation means in relation to the reference position means;

calculating with the calculation means a fractional pulsed volume of fluid that corresponds to a calculated number of degrees of rotation of the shaft based on a monitored rotational position of the shaft;

causing the shaft to move the calculated number of degrees of rotation so as to discharge said fractional pulsed volume based on the calculated number of degrees of rotation.

2. A system for aspirating and dispensing of fluids comprising in combination a volumetric pump, a motor, a motor shaft, a motor driver, an encoder, and a computing unit operatively associated with a calculation unit; said volumetric pump having a reference position means; the calculation unit being constructed and arranged in relation to the reference position means to translate rotation of the motor shaft into two simultaneous motions, a first motion moving the shaft up and down to displace fluid and a second motion of axially rotating the shaft to move a volume of fluid from an input port to an output port thereby providing continuous fluid volume discharges in quasi-sinusoidal pulses over time upon constant shaft rotation, amounts of said fluid volume discharges being controlled based on calculation of a displaced volume for each degree of rotation of the shaft by the calculation unit with regard to the position of the shaft in relation to the reference position means; said encoder including means for measuring angular displacements of said shaft and means for transferring such data to said computing unit; and wherein said input port is separate from said output port.

3. A system according to claim 2 operated to aspirate and dispense fluid volumes to satisfy pipetting functions in a clinical laboratory.

4. A system according to claim 2 wherein the computing unit is provided with a fluid volume to be displaced by the volumetric pump as an input, and a computed number of revolutions to be provided by the motor driver as an output, and a link between both.

5. A system according to claim 4 wherein the computing unit is provided with a stored relation between incremental angular rotation of the motor shaft and fluid volume moved as a result of said incremental angular rotation, enabling movement of fluid volumes which are only a fraction of a volume moved during one complete revolution of the motor shaft.

6. A system according to claim 5 wherein said volume fraction is generated by an incremental angular rotation of the shaft controlled by the motor driver by means of the computing unit.

7. A system according to claim 6 wherein the motor driver actuates the motor to provide a number of encoder pulses as requested by the computing unit.

\* \* \* \* \*